United States Patent [19]

Slaughter

[11] 4,332,004
[45] May 25, 1982

[54] LIGHTING SYSTEM FOR USE ON A WELDER HELMET

[76] Inventor: Grimes G. Slaughter, 240 N. Purdue Ave., Apt. 211, Oak Ridge, Tenn. 37830

[21] Appl. No.: 193,365

[22] Filed: Oct. 2, 1980

[51] Int. Cl.³ .............................................. F21L 15/14
[52] U.S. Cl. ........................................ 362/105; 2/10; 219/147; 362/106
[58] Field of Search ................. 362/106, 105; 2/8, 10, 2/427; 219/147

[56] References Cited

U.S. PATENT DOCUMENTS

| | | | |
|---|---|---|---|
| 2,045,802 | 6/1936 | Richter | 177/311 |
| 3,227,866 | 1/1966 | Peters | 219/147 |
| 3,792,226 | 2/1974 | Bush | 219/147 |
| 3,890,646 | 6/1975 | Fassett et al. | 2/8 |
| 4,011,594 | 3/1977 | Guilbaud et al. | 2/8 |
| 4,039,803 | 8/1977 | Harsch | 219/147 |
| 4,109,132 | 8/1978 | Butoi | 219/147 |

Primary Examiner—Donald P. Walsh
Attorney, Agent, or Firm—Luedeka & Fitch

[57] ABSTRACT

A lighting system for a welders helmet which includes a high intensity, high Kelvin temperature electric light source attached to the face shield for directing a high energy, high Kelvin temperature light beam forwardly of the viewing port, and an energizing circuit including an on-off switch interconnecting the light source to a source of electrical energy which deenergizes the light source where the welder's eyes are not protected by the face shield.

6 Claims, 4 Drawing Figures

LIGHTING SYSTEM FOR USE ON A WELDER HELMET

BACKGROUND OF THE INVENTION

The present invention relates to a high intensity lighting system for use on welders helmets.

Typical welders helmets have a viewing port which is covered with a light filtering window through which the welding operation is viewed by the welder in order to protect his eyes. The light filtering window must be such that, in essence, little or no light passes through the filtering window until the welding arc is struck and the welding task begun.

A drawback is that before a welding arc is struck, the welder cannot see through the light filtering window. Thus, he cannot see the workpiece and cannot accurately control the exact point at which the arc is to be struck. Even when an arc is struck, there are areas that are not well illuminated by the welding arc. Therefore, the welder cannot adequately see ahead of the welding electrode in the direction in which he must move the electrode.

Attempts have been made to overcome this problem by placing high intensity lamps on stands about the work area. However, this attempted solution has a number of defiencies. For example, the area of illumination provided by the lamps is not immediately controllable by the welder. To position the lamps, he would have to stop welding, lay down the welding apparatus, lift the welding helmet exposing his eyes to the high intensity light and turn off the light, or turn off the light before lifting his helmet, estimate the location he wants illuminated, reposition the lamp, replace helmet over his face and turn on the lamp. And then he may not have aimed the lamp correctly to illuminate the desired area. As the welding progresses to different locations on the work piece, the above procedure would have to be repeated over and over, thus, slowing the welding task which translates into increased costs. Also, this type of lighting system is clumsy and large; and for this reason difficult to move from one job site to another. Furthermore, these lamps do not satisfactorally illuminate a work piece so that it can be viewed clearly through the light filtering window of a welders helmet for the reason that they can not safely be of a high enough intensity without possibly subjecting by-standers to a large area of blinding light. These stand-mounted lamps also crowd the work area and are, therefore, very susceptible to being knocked over and damaged, or injurying by-standers. They also take-up valuable floor space.

SUMMARY OF THE INVENTION

The present invention recognizes these problems and provides a solution which is effective for the intended task, and is relatively inexpensive and straightforward.

An object of the present invention is to provide a high intensity, high Kelvin temperature light source for use with welders helmets. The light source can be used on new helmets or retrofitted to existing helmets.

Another object of the invention is to provide a high intensity, high Kelvin temperature light source which is immediately directionally controllable by the person performing the welding task.

A further object of the invention is to provide a high intensity, high Kelvin temperature light source which automatically turns-off before the welders eyes are exposed.

Yet another object of the invention is to provide a high intensity, high Kelvin temperature light source which does not take-up any floor space in the work area.

Still a further object of the invention is to provide a high intensity, high Kelvin temperature light source which minimizes the possible injury to the eyes of the by-standers.

More particularly, the present invention is a light source for a welders helmet of the type to be worn on the head of a person performing a welding task and having a face shield adapted to be removably positioned over the face of the welder. The face shield has a viewing port and a light filtering window mounted to the face shield for movement between a first position covering the viewing port and a second position uncovering the viewing port. The high intensity, high Kelvin temperature light source is attached to or integrally formed in the face shield for directing a high intensity, high Kelvin temperature beam to a location in front of the viewing port. An electrical energizing circuit is provided for connecting the high intensity, high Kelvin temperature light source to a source of electrical energy. An on-off switch is included in the energizing circuit and is operatively associated with the light filtering window. The on-off switch closes when the light filtering window is in the first position allowing current to flow in the energizing circuit illuminating the high intensity, high Kelvin temperature light source and immediately opens when the light filtering window is initially moved toward the second position preventing current flow in the energizing circuit shutting off the high intensity, high Kelvin temperature light source.

The high temperature, high Kelvin temperature light source can also be used with a welders helmet of the type worn on the welders head and having a headband with a face shield pivotally mounted thereto for movement between a first position covering the face of the person and a second position uncovering the face of the person. The face shield includes a viewing port covered by a fixed position light filtering window. A high intensity, high Kelvin temperature light source is attached to or integrally formed with the face shield for directing a high intensity, high Kelvin temperature light beam to a location in front of the face shield. An electrical energizing circuit is provided for connecting the high intensity, high Kelvin temperature light source to a source of electrical energy. An on-off switch is included in the energizing circuit and is operatively associated with the pivot mounting of the face shield to the head band. The on-off switch closes when the face shield is in the first position allowing current to flow in the energizing circuit illuminating the high intensity, high Kelvin temperature light source and immediately opens when the face shield is initially moved toward the second position preventing current flow in the energizing circuit shutting off the high intensity, high Kelvin temperature light source.

BRIEF DESCRIPTION OF THE DRAWING

A more complete understanding of the present invention will be had with reference to the specification and accompanying drawing wherein like numerals refer to like parts throughout and in which.

DETAILED DESCRIPTION

Figure 1:
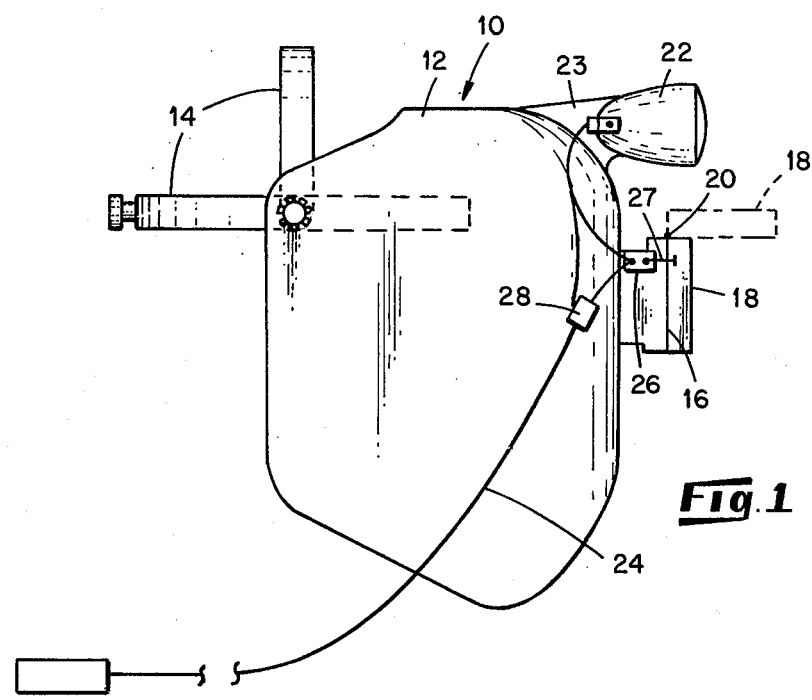
FIG. 1 illustrates a high intensity, high Kelvin temperature light source used with, for example, one type of welders helmet.

FIG. 1 illustrates a welders helmet, generally denoted as the numeral 10, which has a face shield 12 adapted to be removably positioned over the face of a person performing a welding task. Typically, the face shield is attached to a head band 14 which fits about the head of the welder. A viewing port 16 is formed in the face shield 12 to provide the welder with a view through the face shield when the face shield is positioned over his face. A light filtering window 18 is provided to protect the eyes of the welder from being burned or otherwise injured while welding. The light filtering window 18 is pivotally attached to the face shield for movement between a first position covering the viewing port 16, as shown in solid lines in FIG. 1, and a second position away from or uncovering the viewing port 16, as shown in broken lines in FIG. 1. The means for pivotally attaching the light filtering window to the face shield is illustrated as a hinge 20. A high intensity, high Kelvin temperature electric light source 22 on the face shield is oriented for directing a high intensity, high Kelvin temperature light beam to a location in front of or forwardly of the viewing port. It should be clearly understood that the high intensity, high Kelvin temperature light source could be integral with the face shield or be attached to it by attachment means 23 of any convenient design.

The high intensity, high Kelvin temperature electric light source 22 is adapted to be interconnected with a source of electrical energy by means of an energizing circuit, generally denoted as the numeral 24. An on-off switch 26 is located in the energizing circuit and attached to the face shield 12 proximate the viewing port 16. This on-off switch 26 can be of virtually any conventional or otherwise convenient type, but is illustrated as a two-way plunger-type switch, for example, which closes when its plunger 27 is depressed and opens when its plunger 27 is released. As illustrated, a manually operated three way switch 28 is included in the energizing circuit 24. This three way switch 28 has a first or light "on" position, a second or light "off" position and a third position which turns control of the energization of the high intensity, high Kelvin temperature light source over to the on-off switch 26. When the manual switch 28 is in the "on" position electric current will flow to the high intensity, high Kelvin temperature light source and the circuit to the on-off switch 26 is opened, therefore the high intensity, high Kelvin temperature light source will be energized regardless of the position of the on-off switch 26. Likewise, when this manual switch 26 is in the "off" position electric current will not flow to the high intensity, high Kelvin temperature light source and the circuit to the on-off switch 26 is opened, therefore the high intensity, high Kelvin temperature light source will not be energized regardless of the position of the on-off switch 26. When the manual switch 28 is in its third position, the circuit from the manual switch 28 to the high intensity, high Kelvin temperature light source is opened and the circuit to the on-off switch 26 is closed so that the energization and de-energization of the high intensity, high Kelvin temperature light source is under the control of the on-off switch 26. Because of the very high intensity light generated by the high Kelvin temperature light source, the light source itself could temporarily cause blindness or discomfort to the welder wearing the helmet. Therefore, in this embodiment, the on-off switch 26 is attached to the helmet and positioned relative to the light filtering window 18 such that the light filtering window does not contact the plunger 27 of the on-off switch 26 until it is in the first position covering the viewing port 16 at which point it causes the on-off switch 26 to close allowing electric current to flow through the energizing circuit 24 to the high intensity, high Kelvin temperature light source 22 and illuminating it. Thus, the light source 22 will not be illuminated until the welders eyes are protected from the high intensity light generated by the light source. Likewise, the on-off switch 26 is attached to the helmet and positioned relative to the light filtering window 18 such that when the light filtering window 18 is initially pivoted toward the second position away from the viewing port, the plunger of the on-off switch 27 is immediately released causing the on-off switch to open interrupting the flow of electric current to the high intensity light source 22, de-energizing it and shutting it off. Therefore, by the time the welders eyes are exposed, the light source 22 will have been de-energized and the residual light beam will have faded.

The manually operated switch 28 allows the welder to override the switch 26 so that, for example, the welder can turn off the high intensity, high Kelvin temperature light source 22 when he lays the helmet down so that it will not be inadvertently turned on by accidental movement of the light filtering window 18.

Figure 2:
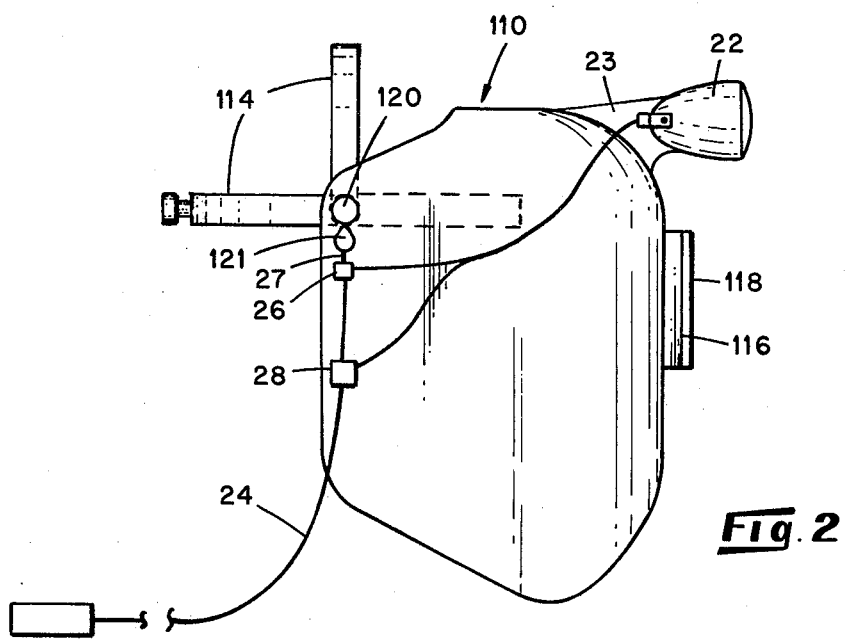
FIG. 2 illustrates a high intensity, high Kelvin temperature light source used with another type of welders helmet.

FIG. 2 illustrates the high intensity, high Kelvin temperature light source 22 attached to a somewhat different type of welders helmet, generally denoted as the numeral 110, which has a face shield 112 adapted to be removably positioned over the face of a welder. A head band 114 is provided to fit about the head of the welder. The face shield 112 is attached to the head band by means of a pivot joint 120 so that the face shield 112 can be pivotally moved from a first position covering the welder's face to a second position uncovering the welder's face. The face shield 112 includes a viewing port 116 and a light filtering window 118 fixed over the viewing port to protect the welder's eyes from being burned or otherwise injured while welding. A high intensity, high Kelvin temperature electric light source 22 on the face shield is oriented for directing a high intensity, high Kelvin temperature light beam to a location in front of or forwardly of the viewing port. It should be clearly understood that the high intensity, high Kelvin temperature light source 22 could be integral with the face shield, or attached to it by attachment 23 of any convenient design. The high intensity, high Kelvin temperature light source 22 is adapted to be interconnected with a source of electrical energy by means of an energizing circuit generally denoted as the numeral 24. An on-off switch 26 is located in the energizing circuit and is attached to the face shield 112 proximate the pivot joint 120. The on-off switch 26 can be of virtually any conventional or otherwise convenient type, but is illustrated as a two-way plunger-type switch which closes when its plunger 27 is depressed and opens when its plunger 27 is released. As illustrated, a manually operated three way switch 28 is included in the energizing circuit 24. The three way switch 28 has a first or light "on" position, a second or light "off" position and a third position which turns control of the energization of the high intensity, high Kelvin temperature light source over to the on-off switch 26. When this manual switch 28 is in the "on" position electric current will flow to the high intensity, high Kelvin temperature light source 22 and the circuit to the on-off switch 26 is opened, therefore the high intensity, high Kelvin temperature light source 22 will be energized regardless of the position of the on-off switch 26. Likewise, when this manual switch 28 is in the "off" position electric current will not flow to the high intensity, high Kelvin temperature light source 22 and the circuit to the on-off switch 26 is opened, therefore the high intensity, high Kelvin temperature light source 22 will not be energized regardless of the position of the on-off switch 26. When the manual switch 28 is in its third position, the circuit from the manual switch 28 to the high intensity, high Kelvin temperature light source 22 is opened and the circuit to the on-off switch 26 is closed so that the energization and de-energization of the high intensity, high Kelvin temperature light source 22 is under the control of the on-off switch 26. Further, cam means 121 is associated with the pivot joint 120 for movement as the face shield 112 moves between its first and second positions. The cam means 121 can be of various forms, for example, a short sector cam attached to the pivot joint 120 for movement with the pivot joint 120. Again, the light source 22 generates a very high intensity, high Kelvin temperature light beam which could cause temporary blindness or discomfort to the welder wearing the helmet. Therefore, the on-off switch 26 is located on the face shield proximate the cam means so that the cam means 121 will not contact and depress the plunger 27 of the on-off switch 26 until the face shield is in the first position covering the welder's face at which point the on-off switch 26 is closed allowing electric current to flow through the energizing circuit 24 to the high intensity, high Kelvin temperature light source 22 and illuminating it. Thus, the light source 22 will not be illuminated until the welder's eyes are protected from the high intensity light generated by the high intensity light source. Likewise, the on-off switch 26 is also located with respect to the cam means 121 such that when the face shield is initially pivotally moved toward the second position, uncovering the welder's face, the cam means 121 will immediately move out of contact with and release the plunger 27 of the on-off switch 26 causing the on-off switch 26 to immediately open interrupting the flow of electric current to the high intensity, high Kelvin temperature source 22 de-energizing it and shutting it off. Therefore, by the time the welder's eyes are exposed, the light source 22 will have been de-energized and the residual light will have faded.

The manually operated switch 28 allows the welder to override the switch 26 so that, for example, the welder can turn off the high intensity, high Kelvin temperature light source 22 when he lays the helmet down so that it will not be inadvertently turned on by accidental movement of the face shield.

The high intensity, high Kelvin temperature light source 22 must generate at least as high an intensity light as that generated by the welding arc itself in order to illuminate a field of view perceptible through the light filtering window. The light filtering windows most frequently employed with welders helmets are commercially denoted by the numbers 10, 11 and 12. The light transmission decreases with the increasing numbered light filtering window. The light intensity required to perform three different tasks for each of the three above-mentioned light filtering windows is given in the table below:

| | LIGHT INTENSITY IN FOOT CANDLES REQUIRED TO SEE STATED OBJECTS THROUGH SPECIFIED FILTER WINDOW | | |
|---|---|---|---|
| | Black on White | Brown Rod on Rusty Steel | Newsprint |
| No. 10 filter | 300 | 460 | 800 |
| No. 11 filter | 350 | 2800 | 9050 |
| No. 12 filter | 400 | 6400 | 12800 |

Also, it is important that the high energy light source generate a high Kelvin temperature. It has been determined, for example, that in order to read newsprint through a number 10 filter window a frosted light bulb producing relatively low Kelvin temperature on the order of 2500-3000 degrees K. had to produce almost 6000 foot candles as compared to about 800 foot candles using a light source generated by higher Kelvin temperatures.

In practice, it has been found that a preferred high intensity light source 22 should generate a high Kelvin temperature, for example, on the order of at least 3400 degrees Kelvin and produce a light beam two to three inches in diameter of at least 9000 candlepower. Such a light source can be halogen cycle tungsten lamp having a deep parabolic reflector two to three inches in diameter.

Figure 3:
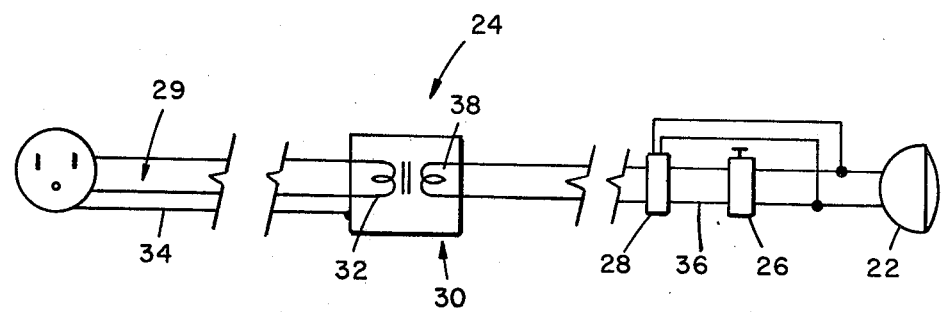
FIG. 3 schematically represents an energizing circuit for the high intensity, high Kelvin temperature light source; and, FIG. 4 schematically represents another energizing circuit for the high intensity, high Kelvin temperature light source.

Now with reference to FIG. 3, there is shown in schematic form an energizing circuit 24 for use with a source of alternating current. This energizing circuit includes a first electric current carrying lead 29 adapted to be electrically connected to a source of A.C. electrical energy, a transformer 30 having its primary coil 32 electrically connected to the first electrical current carrying lead 29, ground means 34 interconnecting the source of A.C. electrical energy and the transformer 30, and a second electric current carrying lead 36 interconnecting the secondary coil 38 of the transformer 30 and the high intensity electric light source 22. The on-off switch means 26 is electrically interconnected to the second electric current carry lead 36 between the secondary coil 38 of the transformer 30 and the high intensity electric light source 22, and the three position switch 28 is also in the second current carrying lead 36 and connected in parallel with the on-off switch 26 to the high intensity, high Kelvin temperature light source 22.

The transformer 30 isolates the light source 22 and the welder from the high voltage of the source of A.C. energy.

Figure 4:
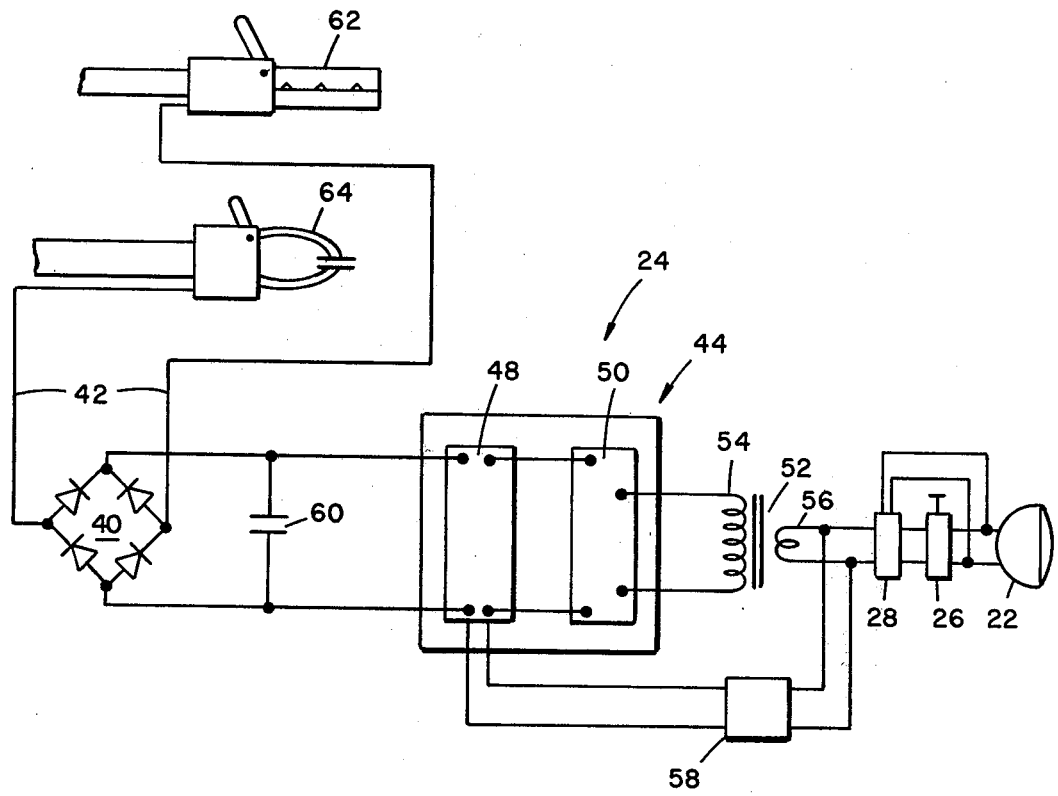

FIG. 4 illustrates in schematic form an energizing circuit 24 which can be used with either an A.C. source of energy or a D.C. source of energy of either positive or negative polarity. The energizing circuit 24 includes a full wave rectifier 40 adapted to be electrically connected to a source of electrical energy by, for example, electric current carrying leads 42. Power conditioning circuit means 44 are also included in the energizing circuit 24. This power conditioning circuit 44 comprises a D.C. to D.C. converter 48 electrically connected to the output of the full wave rectifier means 40 for regulating the voltage, a D.C. to A.C. inverter 50 electrically connected to the D.C. to D.C. converter 48, and a transformer 52 having its primary coil 54 electrically connected to the output side of the D.C. to A.C. inverter 50 and its secondary coil 56 electrically connected to the high intensity, high Kelvin temperature light source 22. The energizing circuit 24 further includes voltage feedback means 58 electrically interconnecting the secondary coil 56 of the transformer 52 and the D.C. to D.C. converter 48 for controlling the voltage fluctuations to the primary coil 54 of the transformer 52 to obtain a relatively constant A.C. voltage to the high intensity, high Kelvin temperature light source 22. Also included in the energizing circuit is a smoothing capacitor 60 electrically connected between the full wave rectifier 40 and the D.C. to D.C. converter 48 for passing a relatively constant voltage to the D.C. to D.C. converter 48. The on-off switch means 26 is electrically associated with the energizing circuit between the secondary coil 56 of the transformer 52 and the high intensity light source 22, and the three position switch 28 is also electrically associated with the circuit between the secondary coil 56 and the high intensity light source 22 and connected to the high intensity, high Kelvin temperature light source 22 in parallel with the on-off switch 26.

It should be understood, that the D.C. to D.C. converter 48 could be directly interconnected between the rectifier 40 and the high intensity, high Kelvin temperature light source 22 through the three position switch 28 and on-off switch means 26.

The energizing circuit could be connected directly to a source of electrical energy or, as depicted in FIG. 4, it could be electrically connected to a welding rod electrode holder 62 and a welding ground clamp 64.

The foregoing detailed description is given primarily for a clearness of understanding and no unnecessary limitations should be understood therefrom for modifications will be obvious to those skilled in the art upon reading this disclosure and can be made without departing from the spirit of the invention of the scope of the appended claims.

I claim:

1. A lighting system for use with a welders helmet of the type having a face shield adapted to cover the face of a person performing a welding task, a viewing port formed in the face shield and a light filtering window covering the viewing port through which the person can view the work piece without exposing his eyes to the welding arc, and pivotal means for moving said light filtering window from the view of the person comprising:
   a high intensity, high Kelvin temperature light source on said helmet and oriented for directing a high intensity, high Kelvin temperature light beam to a location forwardly of said viewing port;
   an energizing circuit for connecting said high intensity, high Kelvin temperature light source to a source of electrical energy, said energizing circuit including a transformer isolating said source of electrical energy from said light source;
   on-off switch means in said energizing circuit for allowing the flow of electrical current from the source of electrical energy of said high intensity, high Kelvin temperature light source when the light filtering window is covering the welder's eyes;
   manually operated switch means in said energizing circuit for selectively overriding the functioning of said on-off switch means; and
   and switch means responsive to pivotal movement of said window from the view of the welder for immediately interrupting the flow of electrical current from the source of electrical energy to said high intensity, high Kelvin temperature light source when the light filtering window is initially moved away from the position covering the welder's eyes so that the light generated by said high Kelvin temperature light source has faded before the welder's eyes are exposed.

2. The lighting system of claim 1 wherein the light filtering window is pivotally mounted on the face shield for movement between a first position covering the viewing port and a second position uncovering the viewing port, and said on-off switch means is operatively associated with and activated by initial pivotal movement of said light filtering window from said first position.

3. The lighting system of claim 1, wherein said operative association of said on-off switch means with the pivot mounting comprises cam means associated with the pivot mounting for movement therewith as the face shield moves between the first and second positions, for activating said on-off switch means to a closed position when the face shield is in the first position and to an open position as the face shield is initially moved toward the second position.

4. The lighting system of claim 1, wherein said energizing circuit comprises:
   a first electric current carrying lead adapted to be electrically connected to a source of A.C. electrical energy;
   a transformer having its primary coil electrically connected to said first electrical current carrying lead;
   ground means interconnecting the source of A.C. electrical energy and said transformer;
   a second electric current carrying lead interconnecting the secondary coil of said transformer and said high intensity electric light source; and,
   said on-off switch means being electrically connected to said second electric current carrying lead between the secondary coil of the transformer and said high intensity electric light source.

5. The lighting system of claim 1, wherein said energizing circuit comprises:
   a full wave rectifier adapted to be electrically connected to a source of electrical energy;
   a transformer;
   power conditioning circuit means electrically interconnecting the output side of said full wave rectifier and the primary coil of said transformer for regulating voltage and sending electrical currents of alternating polarity to the primary coil of said transformer;
   said high intensity electric light source being electrically connected to the secondary coil of said transformer; and,
   said on-off switch means electrically interconnecting the secondary coil of said transformer and said high intensity, high Kelvin temperature electric light source to control the flow of electric current from the secondary coil of said transformer to said high intensity electric light source.

6. The lighting system of claim 5, wherein said power conditioning circuit means comprises:
   a D.C. to D.C. converter electrically connected to the output side of said full wave rectifier for regulating voltage;
   a D.C. to A.C. inverter electrically interconnecting said D.C. to D.C. converter and the primary coil of said transformer;
   voltage feedback means electrically interconnecting the secondary coil of said transformer and said D.C. to D.C. converter for controlling voltage fluctuations to the primary coil of the transformer; and,
   a smoothing capacitor electrically connected between said full wave rectifier and said D.C. to D.C. converter for passing a relatively constant voltage to said D.C. to D.C. converter.

* * * * *

UNITED STATES PATENT AND TRADEMARK OFFICE
CERTIFICATE OF CORRECTION

PATENT NO. : 4,332,004
DATED : May 25, 1982
INVENTOR(S) : Grimes G. Slaughter

It is certified that error appears in the above—identified patent and that said Letters Patent is hereby corrected as shown below:

Column 4, line 62, before "23" insert -- means --

Column 7, line 68, after energy, "of" should be -- to --

Signed and Sealed this

Third Day of August 1982

[SEAL]

Attest:

GERALD J. MOSSINGHOFF

Attesting Officer

Commissioner of Patents and Trademarks